United States Patent
Pinna et al.

(10) Patent No.: US 6,444,215 B1
(45) Date of Patent: Sep. 3, 2002

(54) PLASTER FOR REMOVING COMEDONES FROM THE SKIN

(75) Inventors: Fausto Pinna, Milan; Marco Pinna, Olona, both of (IT)

(73) Assignee: BIOFARM S.r.l., Milan (IT)

( * ) Notice: Subject to any disclaimer, the term of this patent is extended or adjusted under 35 U.S.C. 154(b) by 0 days.

(21) Appl. No.: 09/600,873

(22) PCT Filed: Jan. 22, 1999

(86) PCT No.: PCT/EP99/00426

§ 371 (c)(1),
(2), (4) Date: Aug. 11, 2000

(87) PCT Pub. No.: WO99/40885

PCT Pub. Date: Aug. 19, 1999

(30) Foreign Application Priority Data

Feb. 11, 1998 (IT) .......................................... MI98A0260

(51) Int. Cl.⁷ ............................................. A01N 25/34
(52) U.S. Cl. .................... 424/402; 424/78.03; 424/401; 424/443; 424/448; 604/289; 604/290
(58) Field of Search ............................ 424/78.03, 78.35, 424/78.37, 59, 402, 401, 448, 443, 487, 446; 428/533; 524/48, 53; 604/289, 290

(56) References Cited

U.S. PATENT DOCUMENTS

| | | | | |
|---|---|---|---|---|
| 3,914,524 A | * | 10/1975 | Monte | 428/533 |
| 4,105,824 A | * | 8/1978 | Monte | 428/355 CP |
| 4,231,803 A | * | 11/1980 | Bovier et al. | 106/162.1 |
| 5,512,277 A | * | 4/1996 | Uemura et al. | 424/401 |
| 5,935,596 A | * | 8/1999 | Crotty et al. | 424/401 |
| 5,985,300 A | * | 11/1999 | Crotty et al. | 424/401 |
| 5,993,838 A | * | 11/1999 | Crotty et al. | 424/402 |
| 6,042,844 A | * | 3/2000 | Ishida et al. | 424/443 |
| 6,190,683 B1 | * | 2/2001 | Hoshi et al. | 424/400 |
| 6,306,382 B1 | * | 10/2001 | Uemura et al. | 424/402 |

FOREIGN PATENT DOCUMENTS

EP 0 303 445 * 2/1989

* cited by examiner

Primary Examiner—John G. Weiss
Assistant Examiner—Linh Truong
(74) Attorney, Agent, or Firm—Oblon, Spivak, McClelland, Maier & Neustadt, P.C.

(57) ABSTRACT

Plaster at least partially covered with a layer of dextrin and/or casein and/or starch having an amylopectin content of at least 80%, which when moistened is made to adhere to the skin on which comedones are present, these being removed when the plaster is itself removed after the layer has dried.

1 Claim, 1 Drawing Sheet

PLASTER FOR REMOVING COMEDONES FROM THE SKIN

This invention relates to a plaster able to remove comedones from the skin of a person's face.

It is well known that comedones in the form of small fat deposits situated at the opening of the sebaceous glands form on the facial skin, in particular on the skin of the nose, the chin, the cheek bones and the forehead. These comedones also appear as keratotic plugs in the form of blackheads originating from the keratinization of dead epidermal cells with the sebaceous material and with traces of dirt which blocks the pores of the skin.

Comedones or blackheads represent a skin problem of considerable aesthetic importance, in particular for women. Currently, they are partially removed by the use of detergents or other chemical products, or—more commonly—by squeezing or stretching the skin on the two opposite sides of each comedo.

U.S. Pat. No. 5,512,277 describes polymeric compositions which, when applied to the skin, bind to the dirt and to the keratotic plugs present on the skin, to remove them, when the compositions are themselves removed.

The polymeric compositions illustrated in U.S. Pat. No. 5,512,277 are very complicated and costly, and have the drawback of being chemical products to be applied to the most delicate and exposed portions of the human skin (nose and face).

The main object of this invention is to provide a device of very simple structure and use, which is of low cost and enables comedones to be very effectively removed from the skin using absolutely non-toxic natural products which are innocuous to the skin.

These and further objects are attained by a plaster consisting of a flexible resistant support, one surface of which is at least partly covered with an adhesive layer comprising one or more components, either alone or mixed together, chosen from the group consisting of dextrin, casein and starch having an amylopectin content of at least 80% by weight, said adhesive layer being covered and protected by a thin anti-adhesive film.

The adhesive layer components are natural products (even though they can be produced industrially), commonly used as foods.

Starch is a substance present in many natural products, in which it is in the form of a mixture of amylose and amylopectin in a wide range of percentage ratios depending on the type of natural product in which the starch is present. For example, in common maize the starch is formed from 23% to 27% of amylose and 73% to 77% of amylopectin, and in potato flour from 18% to 22% of amylose and from 78% to 82% of amylopectin, whereas in a particular type of maize, known as waxy maize, the amylose content is only between 4% and 6% whereas the amylopectin content is very high, between 94% and 96%.

Casein is a protein substance (phosphoroprotein) obtained from cow's milk.

Dextrin is a white amorphous substance obtained by hydrolyzing starch and used as an adhesive and agglutinate. Dextrin is widely used in the printing and paper field to form the adhesive part of envelopes, stamps and the like.

When in its pure state, dextrin is a white powder and can be fixed onto the most various supports by being dissolved in water and then applied to such supports by silk-screen printing, by spreading with a doctor blade, or by spraying.

When dry on the support to which it has been applied, dextrin is in the form of a hard film which again becomes adhesive when moistened with water or an aqueous solution.

The aforesaid considerations regarding dextrin are also valid for casein and starches in general.

It has been surprisingly found that if a flexible support carrying on its surface an adhesive layer of dextrin and/or casein and/or starch having an amylopectin content of at least 80% (or alternatively pure amylopectin), either individually or in any mixture, is applied to the skin (in particular a person's face or nose) after having been moistened or after the surface of the skin on which the adhesive layer is to adhere has been wetted, and if the adhesive is left to dry or harden, it adheres to the skin and attaches itself in a sufficiently strong manner to the keratin part of the blackheads or to the free surfaces of the comedones, such that when said support is subsequently removed from the skin the comedones or blackheads are themselves easily removed, as if they were plugs, to remain adhering to the support by the action of the aforesaid specific adhesive.

It has been attempted to achieve the same result by using other natural substances instead of the aforestated, however it has been surprisingly found that only dextrin, casein and amylopectin are effective in attaining the desired object.

For the flexible resistant support, all those materials commonly used to form plasters can be used, such as thin sheets of PVC, polyurethane, polyester, cotton, non-woven fabric (the surface of which can be previously treated with known substances to prevent excessive penetration of the adhesive into the fibrous content of the fabric), paper and the like. The adhesive can be applied to the support in sheet or reel form by common rotogravure or offset printing systems or other systems.

The removable protection film for the adhesive layer can be a film of a plastic or cellulose material treated with anti-adhesive products (polymerized silicones or the like).

The invention will be more apparent from the description of some embodiments thereof given hereinafter by way of non-limiting example with reference to the accompanying drawing, showing a plaster of which:

Figure 1:
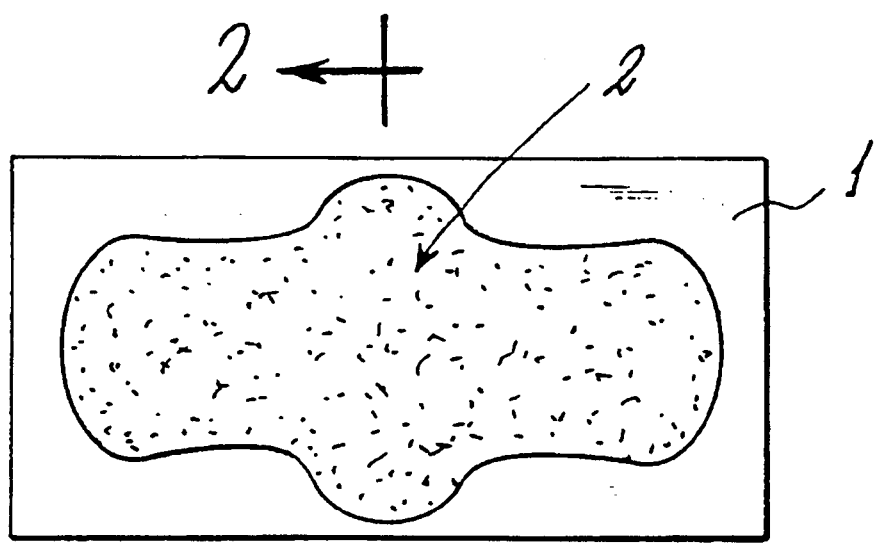
FIG. 1 is a front view.
Figure 1:
Figure 2:
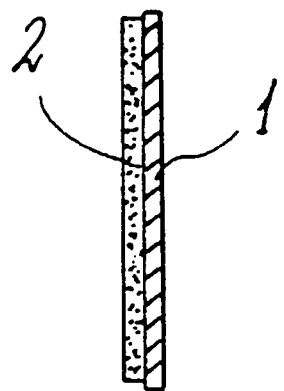
FIG. 2 is a cross-section on the line 2—2 of FIG. 1.

The figures show a plaster comprising a thin flexible support 1, formed for example from a common non-woven fabric of polyester and viscose, having a weight of between 30 and 90 g/m$^2$, preferably 50 g/m$^2$, and a thickness of between 0.7 mm and 1 mm. This support material is used to prepare sheets of useful format for silk-screen printing, for example having a size of 70×100 cm.

A layer of adhesive 2, of which some possible compositions are given hereinafter by way of example, is then applied to the flexible support 1.

EXAMPLE 1

Starch-based Adhesive Composition 80 kg of starch (having an amylopectin content of about 90–95%) partly hydrolyzed to dextrin (with 10% moisture content) are mixed with 320 kg of water at 80–90° C. in a steam-heating jacketed vessel provided with a stirrer of variable speed between 15 and 200 r.p.m., mixing being continued until the starch is completely dissolved, by gradually increasing the temperature to about 95° C. over about 1–2 hours. A clear, very light caramel coloured solution is obtained.

Four separate equal fractions of this solution are separated, each weighing 100 kg.

0.2 kg of nonyl phenyl ethoxylate (as surfactant) and 2 kg of bidistilled glycerol VP are added to a first of these solution portions; 0.2 kg of surfactant and 2 kg of triethyleneglycol are added to a second solution portion (also of 100 kg as the other portions); 0.2 kg of surfactant and 3 kg of sorbitol in 70% solution for food use are added to a third portion; 0.2 kg of surfactant and 3 kg of glucose in 70% solution are added to the forth portion.

Using a common bonding-spreading machine, each of the four different aforedescribed solutions is spread onto the surface of a continuous web (width 48 cm) of single-coated paper of weight 137 g/m$^2$ siliconed on one face. Spreading is carried out at 35–45° C. using a smooth rotating bar acting on the siliconed face of the support. The solutions are partially dried by passage over a steam-heated roller (to 90–120° C.), after which the described web is bonded to a non-woven fabric web of 60 g/m$^2$ with slight calendering prior to winding the combined web obtained in this manner, and on which the quantity of dry adhesive can vary from 30 to 60 g/m$^2$. The described combined web is cut into sheets of 48×70 cm, from which plasters are punched out and are applied to those parts of the face (in particular the nose, chin and forehead) where "blackheads" are present, these being largely easily removed, and most effectively when the adhesive has been obtained from the fourth aforedescribed composition.

EXAMPLE 2
Casein-based Adhesive Composition

Using the apparatus described in Example 1 but employing as heating fluid only hot water at a maximum temperature of 85° C. (to prevent overheating of the casein solutions), 350 kg of hot water at 50° C., 110 kg of powdered casein, 0.2 kg of antifoaming agent (for example emulsified pine oil) and 14 kg of a 30% solution of sodium hydroxide (or 11 kg of sodium tetraborate decahydrate) are mixed together.

The powdered casein and the other said products are added to the hot water in rapid sequence by sprinkling, after which the mixture is left stirring for about 1 hour at a maximum temperature of 60° C. A viscous solution is obtained which is spread and bonded onto a support in the same manner as described in Example 1.

The plasters obtained in Example 2 demonstrated considerable effectiveness in removing comedones from the facial skin. The best result was obtained when sodium tetraborate decahydrate was added to the casein.

EXAMPLE 3
Adhesive Composition based on Mixed Casein and Dextrin

Using the already described apparatus and operating at a maximum temperature of 50° C. to prevent excessive depolymerization, 350 kg of hot water (at 50° C.) are mixed with 60 kg of powdered casein, 20 kg of partially hydrolyzed (10% moisture content) powdered starch (containing at least 80 of amylopectin), 11 kg of sodium tetraborate decahydrate, 0.2 kg of antifoaming agent (for example emulsified pine oil) and 5 kg of powdered mica (5–10 micron granules) to facilitate drying and provide optimum planarity to the product spread on the support.

With this solution a plaster is obtained providing excellent elimination of blackheads or comedones from the facial skin surface.

The same optimum functional characteristics are obtained if 60 kg of partly hydrolyzed starch are used instead of the 60 kg of casein, together with 20 kg of casein instead of the aforesaid 20 kg of partly hydrolyzed starch of this example.

The various solutions described in the aforesaid examples can also be applied in different ways to the respective flexible supports, for example by classical silk-screen printing, using a medium-mesh frame, such as to apply between 40 and 90 g/m$^2$ of dry mixture on the support sheet.

The silk-screened emulsion is then dried in an oven by the normal methods used in silk-screen printing.

The silk-screened sheets are then punched to the desired shape and the plasters obtained are then packaged in heat-bonded packs.

It should be noted that if a very absorbent non-woven fabric (tending to absorb too much water) is used as the support, it is advisable to firstly (before applying the adhesive solution) pass it through nitrocellulose diluted in a solvent (20% of solvent) which, when dried in an oven, forms a transparent layer making the support more impermeable.

The adhesive solution can also be applied to the support by a rotogravure printing machine, which enables the solution mixture to be spread on the support by a doctor blade and roller. In this case the support material is used in a reel instead of in sheets. The reel is automatically unwound by the machine, which passes the support material under the doctor blade, which then deposits the adhesive solution in the desired quantity, after which a roller distributes it uniformly, and an in-line oven dries the mixture (at a temperature of 70° C. for 30 seconds) to enable the reel to be re-wound, and which, if desired, can be punched directly to the required shape.

The individual plasters obtained in the aforedescribed manner are used for example by applying them to the skin of the nose after previously moistening the layer of adhesive substance or after moistening the skin of the nose or face. The moisture dissolves the substance and makes it adhesive.

The plaster is left on the skin for about 10–12 minutes so that the adhesive substance dries, after which the plaster is delicately removed, those comedones or blackheads which were present on the skin portion to which the plaster had been applied remaining attached to the plaster.

What is claimed is:

1. A method for removing comedones from the skin of a persons face, which comprises applying to the skin a plaster comprising a flexible resistant support, one surface of which is at least partially covered with an adhesive layer of a material comprising at least one component selected from the group consisting of amylopectin, starch having amylopectin content of at least 80%, casein and dextrin; and water wherein said layer of material is remoistened at the time when it is applied to the persons skin.

* * * * *